United States Patent
Seo et al.

(10) Patent No.: US 10,137,203 B2
(45) Date of Patent: Nov. 27, 2018

(54) HER2 APTAMER-ANTICANCER DRUG COMPLEX FOR CANCER CELL CHEMOTHERAPY

(71) Applicant: KOREA UNIVERSITY RESEARCH AND BUSINESS FOUNDATION, Seoul (KR)

(72) Inventors: Jae-Hong Seo, Gwacheon-si (KR); Chang Ill Ban, Pohang-si (KR); Hun-Ho Jo, Busan (KR); Ji-Young Kim, Seoul (KR); Young-Kwan Cho, Ansan-si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 15/407,580

(22) Filed: Jan. 17, 2017

(65) Prior Publication Data
US 2018/0050114 A1    Feb. 22, 2018

Related U.S. Application Data

(62) Division of application No. 15/238,583, filed on Aug. 16, 2016, now Pat. No. 9,950,070.

(51) Int. Cl.
| | |
|---|---|
| *C12N 15/11* | (2006.01) |
| *A61K 47/55* | (2017.01) |
| *A61K 47/48* | (2006.01) |
| *C12N 15/115* | (2010.01) |
| *A61K 31/5365* | (2006.01) |
| *A61K 47/68* | (2017.01) |

(52) U.S. Cl.
CPC .......... *A61K 47/55* (2017.08); *A61K 31/5365* (2013.01); *A61K 47/48092* (2013.01); *A61K 47/6855* (2017.08); *C12N 15/115* (2013.01); *C12N 2310/16* (2013.01); *C12N 2310/351* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 2002/0077306 A1* | 6/2002 | Dinkelborg | A61K 51/0491 514/44 R |
| 2004/0249130 A1* | 12/2004 | Stanton | C12N 15/115 530/350 |
| 2005/0169933 A1* | 8/2005 | Steeves | C07K 16/18 424/178.1 |

FOREIGN PATENT DOCUMENTS

| | | |
|---|---|---|
| KR | 10-2011-0086433 A | 7/2011 |
| KR | 10-2013-0091750 A | 8/2013 |
| WO | WO-2011142970 A2 * | 11/2011 ......... C12N 15/1135 |

OTHER PUBLICATIONS

Sangyong Jon. HER2—Specific Peptide Aptamer Conjugated Magneto-Nanoliposome for Combined Breast Cancer Imaging and Therapy, 2012 Health & Medical Technology R&D, Program final report, Korea.

* cited by examiner

*Primary Examiner* — Ekaterina Poliakova-Georgantas
(74) *Attorney, Agent, or Firm* — Rabin & Berdo, P.C.

(57) ABSTRACT

A method of manufacturing a complex for cancer cell chemotherapy comprises an aptamer preparation step of preparing a nucleic acid aptamer having an aptamer base sequence specifically binding to HER2, and a complex formation step of forming an aptamer-anticancer drug complex by reacting the aptamer prepared in the aptamer preparation step with an anticancer drug.

4 Claims, 12 Drawing Sheets
Specification includes a Sequence Listing.

HER2 APTAMER-ANTICANCER DRUG COMPLEX FOR CANCER CELL CHEMOTHERAPY

CROSS-REFERENCE TO RELATED APPLICATIONS

This is a divisional application of U.S. patent application Ser. No. 15/238,583, filed on Aug. 16, 2016, the entire contents of which are hereby incorporated by reference.

STATEMENT REGARDING SPONSORED RESEARCH OR DEVELOPMENT

This invention was made with Korean Government support of Grant No. H112C1852, awarded by the Korea Health Industry Development Institute, funded by the Ministry of Health & Welfare, Republic of Korea.

BACKGROUND OF THE INVENTION

1. Field of the Invention

The present invention relates to a complex for cancer cell chemotherapy and, more particularly, to a HER2 aptamer-anticancer drug complex for chemotherapy of cancer cells, which includes a nucleic acid aptamer specifically binding to HER2 and an anticancer drug linked with the nucleic acid aptamer, so that HER2-positive breast cancer cells are selectively targeted and killed.

2. Description of the Related Art

Breast cancer is cancer that frequently occurs in women, and many techniques for the accurate diagnosis and treatment of breast cancer are being developed. Typical methods for cancer treatment include surgery, radiation therapy, and chemotherapy, one or more of which may be utilized to treat cancer. Specifically, surgery is a method of removing almost all diseased tissue, and is very effective at removing tumors from specific regions, for example, the breast, colon and skin, but is unsuitable for the treatment of tumors in some regions, such as the spine, or for the treatment of dispersed tumors. Also, radiation therapy is useful in the treatment of acute inflammatory diseases, benign or malignant tumors, endocrine dysfunction, and allergic diseases, and is typically effective at treating malignant tumors, which are composed of rapidly dividing cells. Such radiation therapy has defects, including weakness or loss of function of normal tissue due thereto, as well as the concern about skin disease on the treated regions. Particularly in children, in which the growth of internal organs is progressing, serious side effects such as delayed cognitive development or bone growth disorders may result. Also, chemotherapy is widely useful in the treatment of breast cancer, lung cancer and testicular cancer by disturbing the replication or metabolism of cancer cells, but suffers from side effects induced by systemic chemotherapy used in the treatment of cancer. Furthermore, side effects associated with chemotherapeutic agents are generally exemplified by dose-limiting toxicity (DLT), which dictates caution upon administration of drugs. For these reasons, side effects attributable to chemotherapeutic agents and radiation therapy are regarded as important problems in the treatment of cancer patients.

Meanwhile, based on reports that breast cancer patients who overexpress, as one of human epidermal growth factor reactors, a tyrosine kinase bonded to the surface of a cell membrane, namely HER2 (Human epidermal growth factor receptor 2), which is present in the cell membrane and includes an extracellular region that binds to a ligand and an endocellular region that causes protein activation, have lower disease-free life expectancy and a higher recurrence rate than normal persons, HER2 was established as a representative breast cancer biomarker. Moreover, with the goal of overcoming the side effects of the existing therapeutic methods, targeted therapy, which attacks signaling pathways related to the proliferation of cancer or inhibits angiogenesis so that cancer cells are starved to death, is receiving attention. Hence, research into HER2-targeted breast cancer treatment methods is ongoing (Korean Patent Application Publication No. 10-2013-0091750), but is still incomplete.

SUMMARY OF THE INVENTION

Accordingly, the present invention has been made keeping in mind the above problems encountered in the related art, and the present invention is intended to provide a HER2 aptamer-anticancer drug complex for cancer cell chemotherapy, which is able to effectively kill HER2-positive breast cancer cells.

In addition, the present invention is intended to provide a HER2 aptamer-anticancer drug complex for cancer cell chemotherapy, in which an anticancer drug may be effectively delivered to HER2-positive breast cancer cells by targeting HER2 using an aptamer.

In addition, the present invention is intended to provide a HER2 aptamer-anticancer drug complex for cancer cell chemotherapy, which may effectively treat existing drug-resistant breast cancer.

In addition, the present invention is intended to provide a HER2 aptamer-anticancer drug complex for cancer cell chemotherapy, which is formed via disulfide bonding between an aptamer and an anticancer drug, whereby the complex absorbed into cancer cells is split by glutathione present in the cytosol, and thus the release of the drug to non-target regions may be inhibited.

The present invention is accomplished by exemplary embodiments as follows.

An embodiment of the present invention provides a complex for cancer cell chemotherapy, comprising a nucleic acid aptamer specifically binding to HER2 and an anticancer drug linked with the nucleic acid aptamer.

Also, the complex for cancer cell chemotherapy according to the present invention may be formed via disulfide bonding between the nucleic acid aptamer and the anticancer drug.

Also, in the complex for cancer cell chemotherapy according to the present invention, a thiol group may be introduced to a 3' terminal of the nucleic acid aptamer, and the anticancer drug may be an anticancer drug having a thiol group, and thus the disulfide bonding may be formed between the nucleic acid aptamer and the anticancer drug.

Also, in the complex for cancer cell chemotherapy according to the present invention, the nucleic acid aptamer may have a base sequence of SEQ ID NO:1.

Also, in the complex for cancer cell chemotherapy according to the present invention, the anticancer drug may include DM1.

Also, the complex for cancer cell chemotherapy according to the present invention may be used for the treatment of breast cancer.

Also, the complex for cancer cell chemotherapy according to the present invention may be absorbed into HER2-positive breast cancer cells, so that the disulfide bonding is broken by glutathione present in the cytosol to thus isolate the anticancer drug.

Another embodiment of the present invention provides a method of manufacturing a complex for cancer cell chemotherapy, comprising an aptamer preparation step of preparing a nucleic acid aptamer having an aptamer base sequence specifically binding to HER2, and a complex formation step of forming an aptamer-anticancer drug complex by reacting the aptamer prepared in the aptamer preparation step with an anticancer drug.

Also, in the method according to the present invention, the aptamer preparation step may include forming a nucleic acid aptamer having a base sequence of SEQ ID NO:1 specifically binding to HER2, introducing a thiol group to a 3' terminal of the nucleic acid aptamer, performing 2'-O-methyl modification, and activating a 3' thiol group by reaction with dithiothreitol in a triethylammonium acetate buffer.

Also, in the method according to the present invention, the complex formation step may include providing DM1 dissolved in dimethyl sulfoxide, and reacting the aptamer and DM1 at a ratio of 1:1000 in a potassium phosphate buffer containing dimethyl sulfoxide (DMSO) and ethylenediaminetetraacetic acid (EDTA), thus forming the aptamer-anticancer drug complex.

According to embodiments of the present invention, the following effects may be obtained.

The present invention is effective at killing HER2-positive breast cancer cells.

Also, the present invention is effective at delivering an anticancer drug to HER2-positive breast cancer cells by targeting HER2 using an aptamer.

Also, the present invention is effective at treating existing drug-resistant breast cancer.

Also, according to the present invention, when the complex, which is formed via disulfide bonding between the aptamer and the anticancer drug, is absorbed into cancer cells, it is split by means of glutathione present in the cytosol, thus effectively inhibiting the release of a drug to non-target regions.

BRIEF DESCRIPTION OF THE DRAWINGS

The above and other features and advantages of the present invention will be more clearly understood from the following detailed description taken in conjunction with the accompanying drawings, in which.

DESCRIPTION OF SPECIFIC EMBODIMENTS

Hereinafter, a detailed description will be given of a HER2 aptamer-anticancer drug complex for cancer cell chemotherapy according to the present invention, with reference to the appended drawings. Unless otherwise defined, all terms used herein have the same meaning as commonly understood by one of ordinary skill in the art to which the present invention belongs. If the meaning of the term used herein conflicts with the general meaning thereof, it accords to the definition used herein. In the following description of the present invention, detailed descriptions of known constructions and functions incorporated herein will be omitted when they may make the gist of the present invention unclear. As used herein, when any part "includes" any element, it means that other elements are not precluded but may be further included, unless otherwise mentioned.

According to an embodiment of the present invention, a complex for cancer cell chemotherapy includes a nucleic acid aptamer specifically binding to HER2 and an anticancer drug linked with the nucleic acid aptamer.

As used herein, the term "nucleic acid aptamer" refers to single-stranded DNA or RNA having high affinity and selectivity to a specific target material. The aptamer advantageously exhibits high affinity to a target material compared to an antibody, and high thermal stability to thus enable long-term storage at room temperature, facilitates chemical modification to thus be relatively simply produced at low cost, and may be regenerated within a short time even when degenerated. Hence, in the present invention, a nucleic acid aptamer specifically binding to HER2 upon formation of the complex is adopted. The nucleic acid aptamer may have various aptamer base sequences, which may specifically bind to HER2, but preferably has a base sequence of SEQ ID NO:1. In order to form a complex thereof with the anticancer drug, a thiol group is introduced to the 3' terminal of the nucleic acid aptamer.

As the anticancer drug, any drug may be used so long as it is linked with the nucleic acid aptamer to thus kill cancer cells. Preferably useful is a drug having a thiol group, and more preferably useful is maytansine (a maytansinoid, DM1). Maytansine (DM1) is a drug which is linked to a tubulin protein for forming mitotic spindles in the G2/M phase of a cell cycle so that the function of tubulin is inhibited to induce the formation of abnormal mitotic spindles, thus suppressing the normal arrangement of chromosomes, thereby preventing mitosis and leading to the apoptosis of cancer cells. The 3' terminal of the nucleic acid aptamer is introduced with a thiol group, and as the anticancer drug, an anticancer drug having a thiol group is used, whereby the nucleic acid aptamer and the anticancer drug are linked via disulfide bonding, thus forming a complex. Since HER2, which is overexpressed, is found in breast cancer, the complex includes the nucleic acid aptamer for targeting HER2 to thereby effectively target the breast cancer cells. As for the complex that is formed via disulfide bonding, glutathione, which breaks disulfide bonds, is present in the cytosol but absent from the blood and lymph, and thus the complex of the present invention is absorbed into breast cancer cells and then the anticancer drug is isolated, thereby effectively releasing the drug to cancer cells, rather than non-target regions, ultimately decreasing side effects and increasing the effect of cancer cell apoptosis.

Another embodiment of the present invention addresses a method of manufacturing a complex for cancer cell chemotherapy, including: an aptamer preparation step of preparing a nucleic acid aptamer having an aptamer base sequence specifically binding to HER2, and a complex formation step of forming an aptamer-anticancer drug complex by reacting the aptamer prepared in the aptamer preparation step with an anticancer drug.

In the aptamer preparation step, a nucleic acid aptamer having an aptamer base sequence specifically binding to HER2 is prepared. Particularly, a nucleic acid aptamer having a base sequence of SEQ ID NO:1, specifically binding to HER2, is formed, a thiol group is introduced to the 3' terminal of the nucleic acid aptamer (to substitute OH with SH), and 2'-O-methyl modification is performed, after which the reaction with dithiothreitol in a triethylammonium acetate buffer is carried out, thereby activating the 3' thiol group, yielding the nucleic acid aptamer.

In the complex formation step, the aptamer prepared in the aptamer preparation step is reacted with the anticancer drug, thus forming the aptamer-anticancer drug complex. Particularly, DM1 dissolved in dimethyl sulfoxide is provided, and the aptamer and DM1 are reacted at a ratio of 1:1000 in a potassium phosphate buffer containing DMSO and EDTA, thereby obtaining the aptamer-anticancer drug complex.

Still another embodiment of the present invention addresses a pharmaceutical composition for the treatment of breast cancer, including the above complex for cancer cell chemotherapy.

The pharmaceutical composition for the treatment of breast cancer may include (a) a pharmaceutically effective amount of the above complex for cancer cell chemotherapy; and (b) a pharmaceutically acceptable carrier.

As used herein, the term "pharmaceutically effective amount" may refer to an amount sufficient to achieve the effect of breast cancer therapy.

In the pharmaceutical composition for the treatment of breast cancer, the pharmaceutically acceptable carrier may include those typically used for formulations, and examples thereof may include, but are not limited to, lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, and mineral oil. The pharmaceutical composition for the treatment of breast cancer may further include, in addition to the above components, a lubricant, a humectant, a sweetener, a flavoring agent, an emulsifier, a suspending agent, a preservative, etc.

The pharmaceutical composition for the treatment of breast cancer may be administered orally or parenterally (e.g. intravenous, intraperitoneal, intramuscular, subcutaneous, or topical administration).

The appropriate dose of the pharmaceutical composition for the treatment of breast cancer may vary depending on the formulation method, administration mode, the subject's age, weight, and gender, disease severity, diet, administration time, administration route, excretion rate, and response sensitivity, and doctors who are normally trained may easily determine and prescribe the dose effective for desired treatment.

According to a method that may be easily executed by those skilled in the art to which the present invention belongs, the pharmaceutical composition for the treatment of breast cancer may be formulated together with a pharmaceutically acceptable carrier and/or excipient into a unit dose form, or may be packed in multiple-dose containers. As such, the formulation may be provided in the form of a solution, suspension or emulsion in oil or an aqueous medium, or in the form of an extract, a powder, a granule, a tablet, or a capsule, or may further include a dispersant or a stabilizer.

A better understanding of the present invention may be obtained through the following examples which are set forth to illustrate, but are not to be construed to limit the scope of the present invention.

EXAMPLE 1

Formation of Aptamer (1) A nucleic acid (RNA) aptamer [5'-GGGAGGAC-GAUGCGGGACUGUACGGGGCUCUGUGCAGACGA-CUCGCCCGA-3' (SEQ ID NO:1)] having an aptamer base sequence specifically binding to HER2 was designed, and a thiol group was introduced to the 3' terminal of the nucleic acid aptamer (to substitute OH with SH), followed by 2'-O-methyl modification, thereby increasing the stability of the nucleic acid aptamer.

(2) Thereafter, the nucleic acid aptamer was reacted at room temperature for 15 min with 10 μl of 1.0 M dithiothreitol (DTT) in a 0.1 M triethylammonium acetate (TEAA) buffer, whereby the 3' thiol group was activated, and also, extraction was performed three or more times using ethyl acetate to remove excess DTT.

EXAMPLE 2

Formation of Aptamer-Anticancer Drug Complex (Aptamer-DM1)

The aptamer finally obtained in Example 1 was reacted with an anticancer drug (DM1), thereby manufacturing an aptamer-anticancer drug complex. Particularly, DM1 was dissolved in dimethyl sulfoxide (DMSO) to give a 10 mM stock, and the aptamer-DM1 complex was formed in a 100 mM potassium phosphate buffer (pH 7.0) containing 50% DMSO and 2 mM ethylenediaminetetraacetic acid (EDTA). As such, the aptamer and DM1 were reacted at a ratio of 1:1000 at room temperature for 48 hr.

EXAMPLE 3

Purification of Aptamer and Aptamer-Anticancer Drug Complex

The aptamer, finally obtained in Example 1, and the aptamer-anticancer drug complex, finally obtained in Example 2, were purified through high-performance liquid chromatography (HPLC). Separation was progressed using an Eclipse XDB-C18 column through the gradient of a binding buffer (95% 0.1 M TEAA, 5% acetonitrile) and an elution buffer (50% 0.1 M TEAA, 50% acetonitrile). The peaks of HPLC were analyzed using mass spectroscopy, among which only peaks that matched the molecular weights of the aptamer and the aptamer-anticancer drug complex were selected. The aptamer (Aptamer) and the aptamer-anticancer drug complex (Aptamer-DM1), purified in Example 3, were used for the following Examples.

EXAMPLE 4

Culture of Breast Cancer Cell Lines and Evaluation of Expression of HER2 in Breast Cancer Cell Lines (1) Each of breast cancer cell lines, including MCF7, T47D, SKBR3, BT474, MDA-MB-453, and MDA-MB-231, was cultured under conditions of 5% $CO_2$ and 37° C. in a Dulbecco's modified Eagle's medium (DMEM) containing 10% fetal bovine serum (FBS), streptomycin-penicillin (100 U/ml) and Fungizone (0.625 μg/ml).

(2) The cells cultured on 8-well chamber slides were fixed with 4% paraformaldehyde, washed with PBS, and cultured for 10 min with 0.2% Triton X-100. Thereafter, the cells were cultured overnight at 4° C. with primary antibodies in an antibody dilution buffer and then cultured at room temperature for 2 hr with fluorescence-conjugated secondary antibodies. Thereafter, the cells were mounted on ProLong Gold Antifade Reagent containing DAPI (4',6'-diamidine-2'-phenylindole dihydrochloride). Particularly, each of the cultured breast cancer cell lines was subjected to immunocytochemistry (ICC) using a HER2 antibody, the nucleus thereof was stained with DAPI, and HER2 (red) and nucleus (blue) regions were imaged using a confocal microscope. The results are shown in FIG. 1.

Figure 1:
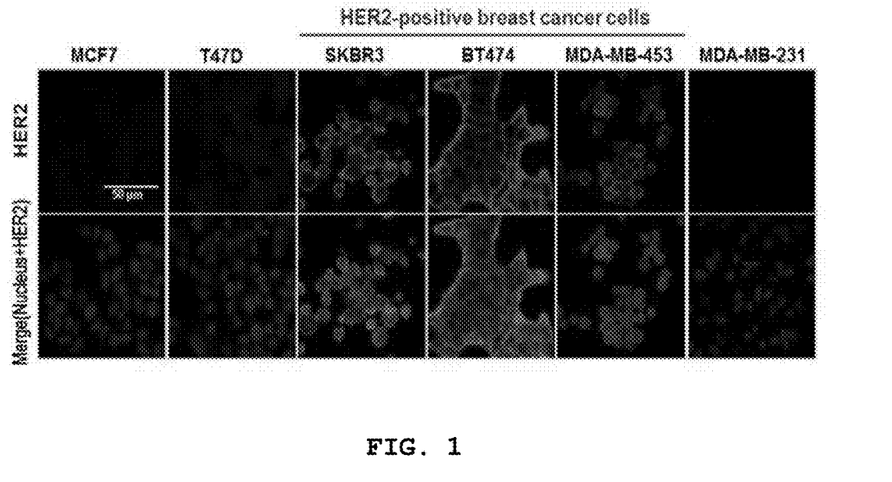
FIG. 1 shows confocal microscopy images depicting the extent of expression of HER2 in different breast cancer cell lines.
Figure 2A:
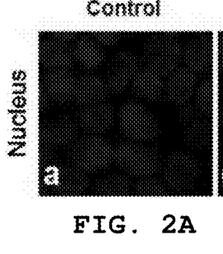
FIGS. 2A to 2L show confocal microscopy images depicting the targeting capability of the complex in the BT474 breast cancer cell line.
Figure 2B:
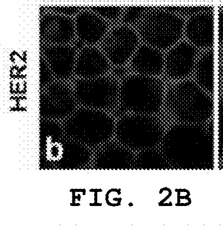
Figure 2C:
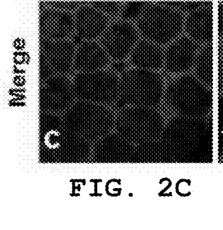
Figure 2D:
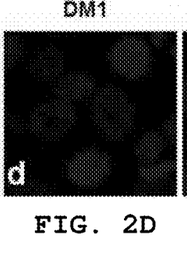
Figure 2E:
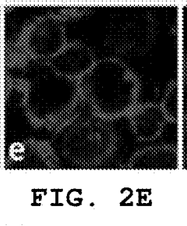
Figure 2F:
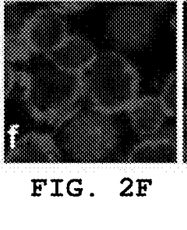
Figure 2G:
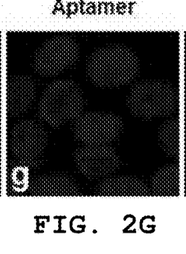
Figure 2H:
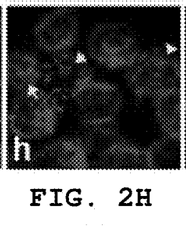
Figure 2I:
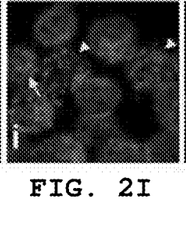
Figure 2J:
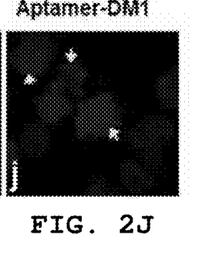
Figure 2K:
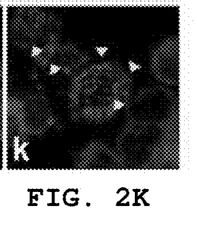
Figure 2L:
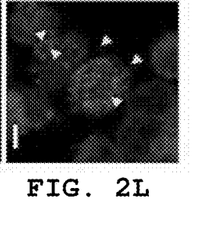

(3) As shown in FIG. 1, HER2 was highly expressed on the cell membranes of the HER2-positive breast cancer cell lines (SKBR3, BT474 and MDA-MB-453), but was hardly expressed on the Luminal type MCF7 and T47D breast cancer cell lines and the Basal type MDA-MB-231 cell line.

EXAMPLE 5

Evaluation of Targeting Capability of Aptamer-Anticancer Drug Complex to HER2-Positive Breast Cancer Cells (1) ICC was performed using the HER2 antibody. The HER2-positive breast cancer BT474 cell line, the nucleus of which was stained with DAPI, was treated with a control (DMSO), DM1, Aptamer, and Aptamer-DM1 at a concentration of 10 nM for 48 hr, and HER2 (red) and the nucleus (blue) were imaged using a confocal microscope. The results are shown in FIGS. 2A to 2L.

Figure 3:
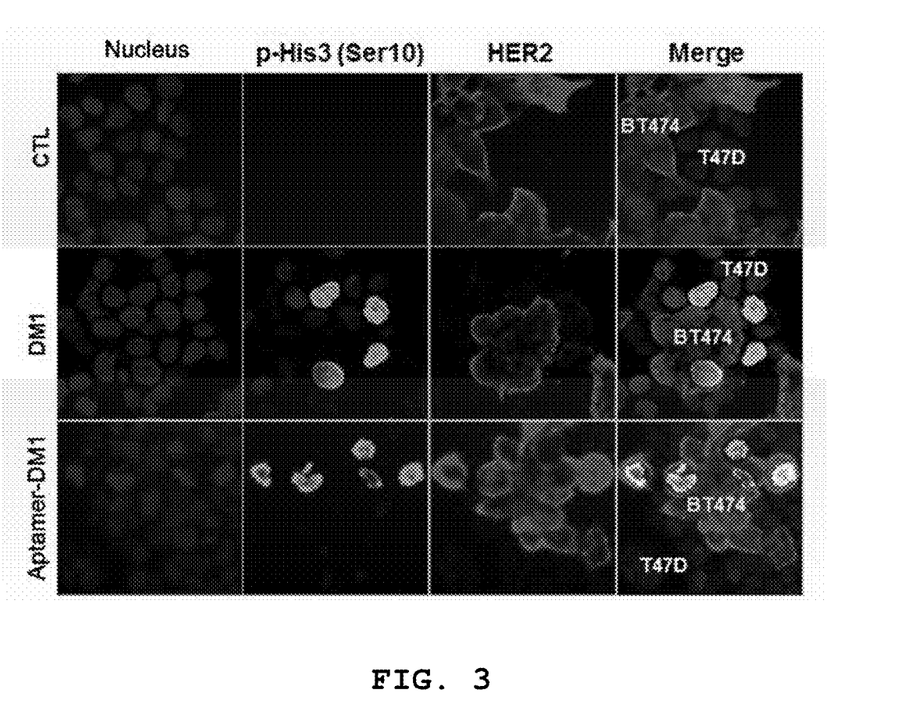
FIG. 3 shows confocal microscopy images depicting the targeting capability of the complex in the HER2-positive breast cancer cell line and the HER2-negative breast cancer cell line, which are co-cultured.
Figure 4:
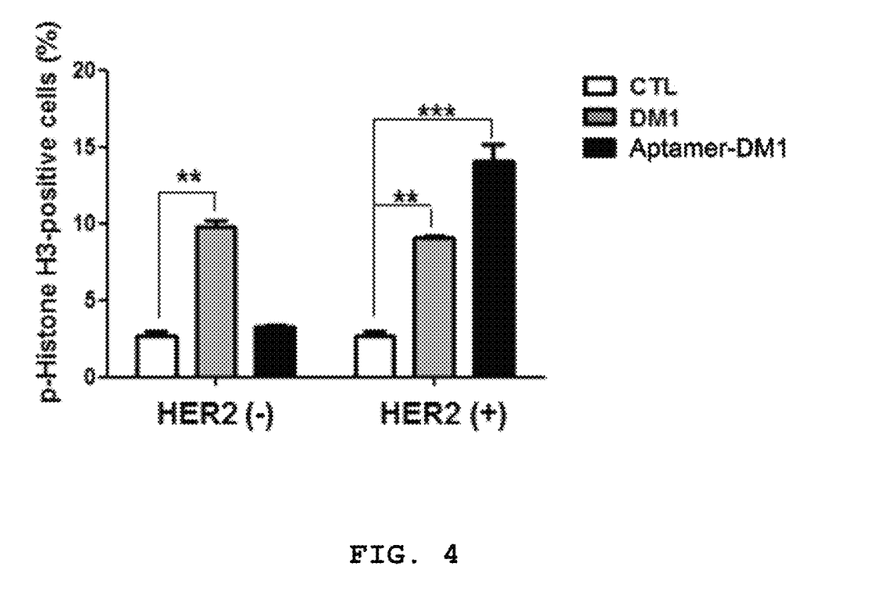
FIG. 4 shows the results of quantification of the number of cells in which His3 is detected depending on whether HER2 is expressed or not.

(2) HER2 and a mitotic arrest marker, namely phospho-Histone H3 (p-His3), were stained with ICC, and the HER2-positive breast cancer BT474 cell line and the HER2-negative breast cancer T47D cell line, the nuclei of which were stained with DAPI, were co-cultured at a ratio of 1:1 and treated with a control (DMSO), DM1, and Aptamer-DM1 at a concentration of 10 nM for 24 hr. Thereafter, the nuclei (blue), p-His3 (green), and HER2 (red) were imaged using a confocal microscope. The results are shown in FIG. 3. The number of cells in which p-His3 was detected was quantified based on whether HER2 was expressed or not. The results are shown in FIG. 4.

(3) As shown in FIGS. 2A to 2L, the expression of HER2 on the cell membrane was observed in the control group and the DM1-treated group (FIGS. 2B, 2C, 2E and 2F), and cellular internalization of HER2 from the cell membrane was observed in the groups treated with Aptamer and Aptamer-DM1 (where cellular internalization of HER2 is represented by yellow arrows, FIGS. 2H, 2I, 2K and 2L). Thereby, Aptamer and Aptamer-DM1 can be seen to specifically recognize HER2 to thus realize cellular internalization.

(4) As shown in FIG. 3, in the control group, the cells in which HER2 was expressed are deemed to be BT474 and the cells in which HER2 was not expressed are deemed to be T47D. In the DM1-treated group, expression of p-His3 was found regardless of whether HER2 was expressed or not, but in the group treated with Aptamer-DM1, p-His3 was detected only in the cells in which HER2 was expressed. As shown in FIG. 4, in the DM1-treated group, the proportions of cells in which p-His3 was detected were not significantly different between the HER2-positive cell line and the HER2-negative cell line. In the group treated with Aptamer-DM1, the proportion of cells in which p-His3 was detected was remarkably increased in the HER2-positive cell line but was considerably decreased in the HER2-negative cell line. This is because Aptamer-DM1, which recognized HER2 of BT474 cells, was introduced into the cytosol, and thus mitotic arrest was induced by the isolated DM1, and simultaneously, the expression of p-His3 was increased, from which Aptamer-DM1 can be confirmed to specifically target only HER2.

EXAMPLE 6

Evaluation of Ability of Aptamer-Anticancer Drug Complex to Selectively Kill HER2-Positive Breast Cancer Cells (1) HER2-positive breast cancer cell lines (SKBR3, BT474, MDA-MB-453) and HER2-negative breast cancer cell lines (MCF7, T47D) were treated with a control (DMSO), DM1, Aptamer, and Aptamer-DM1 at a concentration of 10 nM for 72 hr, after which the cells were acquired and fixed with 95% ethanol containing 0.5% Tween-20 for 24 hr and cultured for 30 min with propidium iodide (PI, 50 μg/ml) and RNase (50 μg/ml). Thereafter, the apoptosis rate (sub-G1%) of cancer cells was measured through DNA content analysis using flow cytometry. The results are shown in FIG. 5.

(2) Typically, the cell cycle includes, depending on the amount of DNA in cells, G1 (cell growth phase)-S (cell replication phase)-G2/M (cell mitotic phase). The induction of apoptosis is accompanied by DNA fragmentation, and thus DNA replication and division become impossible, and the amount of DNA is remarkably decreased compared to the G1 phase. The results of apoptosis are represented by the percentage of sub-G1 in the cell cycle.

Figure 5:
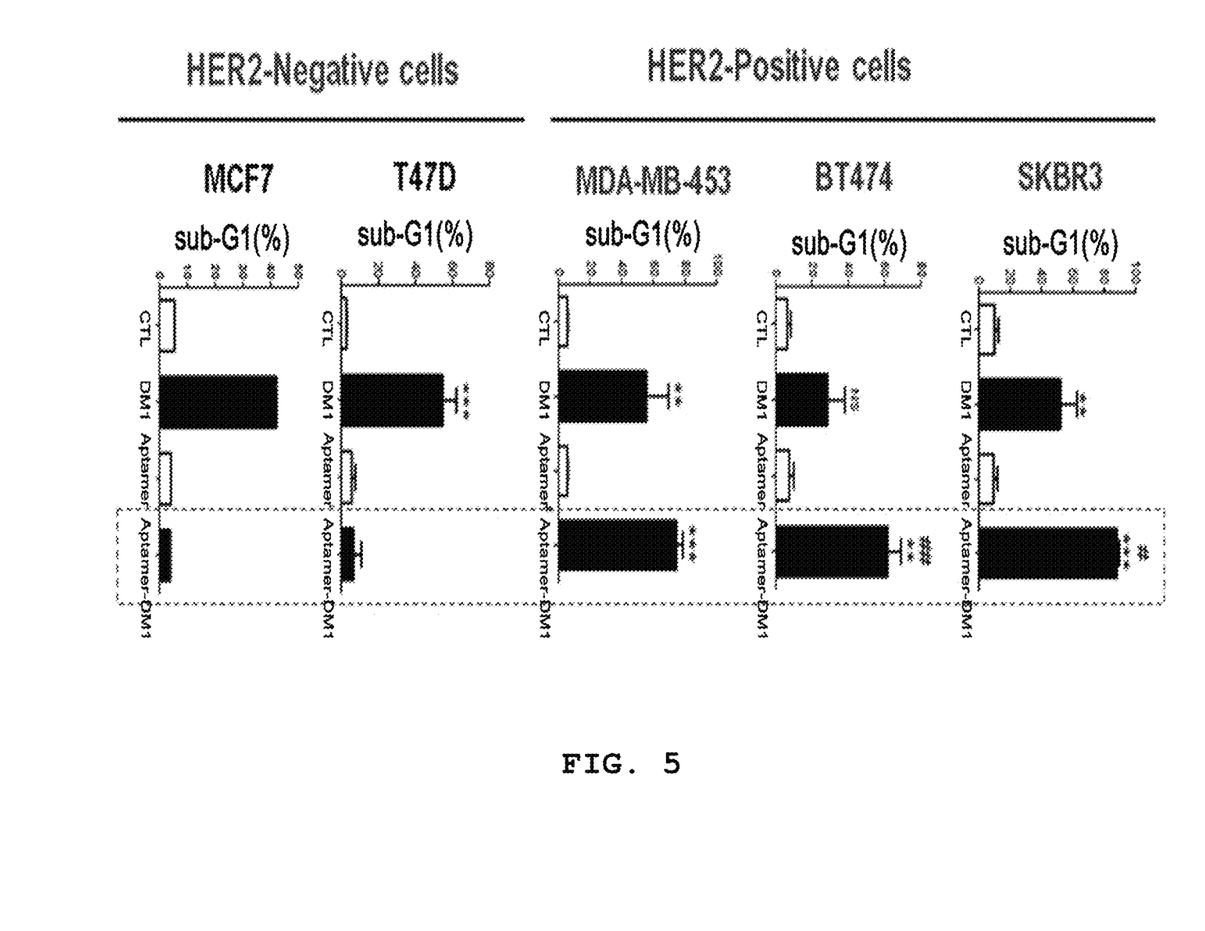
FIG. 5 shows the results of measurement of the ability of the complex to selectively kill HER2-positive breast cancer cells.

(3) As shown in FIG. 5, the control group and the group treated with Aptamer had remarkably low apoptosis rates in all cell lines, but in the DM1-treated group, a relatively high apoptosis rate was induced in all cell lines. In the group treated with Aptamer-DM1, the apoptosis rate was high in the HER2-positive cell lines but low in the HER2-negative cell lines. Also, the group treated with Aptamer-DM1 had a high apoptosis rate in the HER2-positive cell lines compared to the DM1-treated group. Thereby, Aptamer-DM1 can be confirmed to induce specific apoptosis only in the positive breast cancer cell line in which HER2 is expressed and to increase apoptosis through isolation of DM1 in the cells in coincidence with the decomposition of HER2 by the cellular internalization of HER2.

EXAMPLE 7

Figure 6:
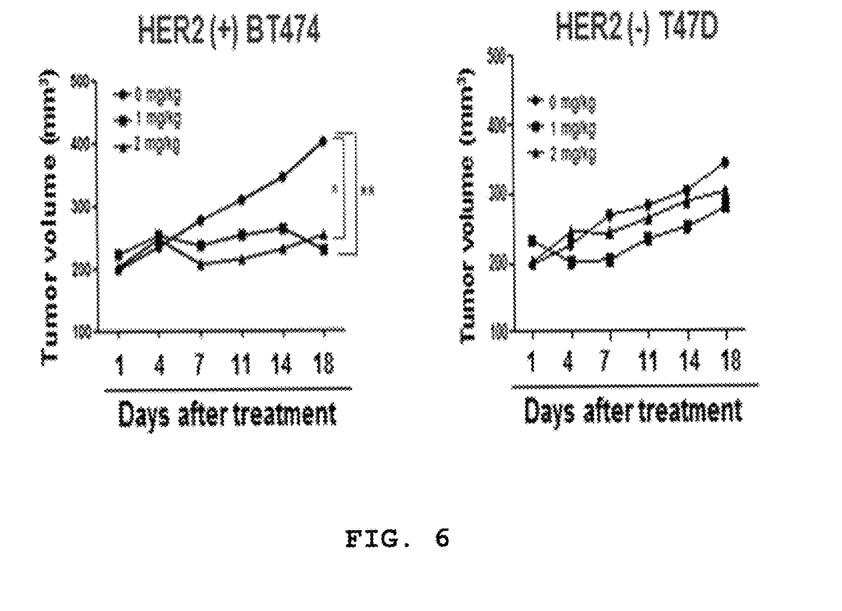
FIG. 6 shows the results of measurement of the tumor volume to evaluate the ability of the complex to selectively kill HER2-positive breast cancer cells in breast cancer disease animal models.
Figure 7:
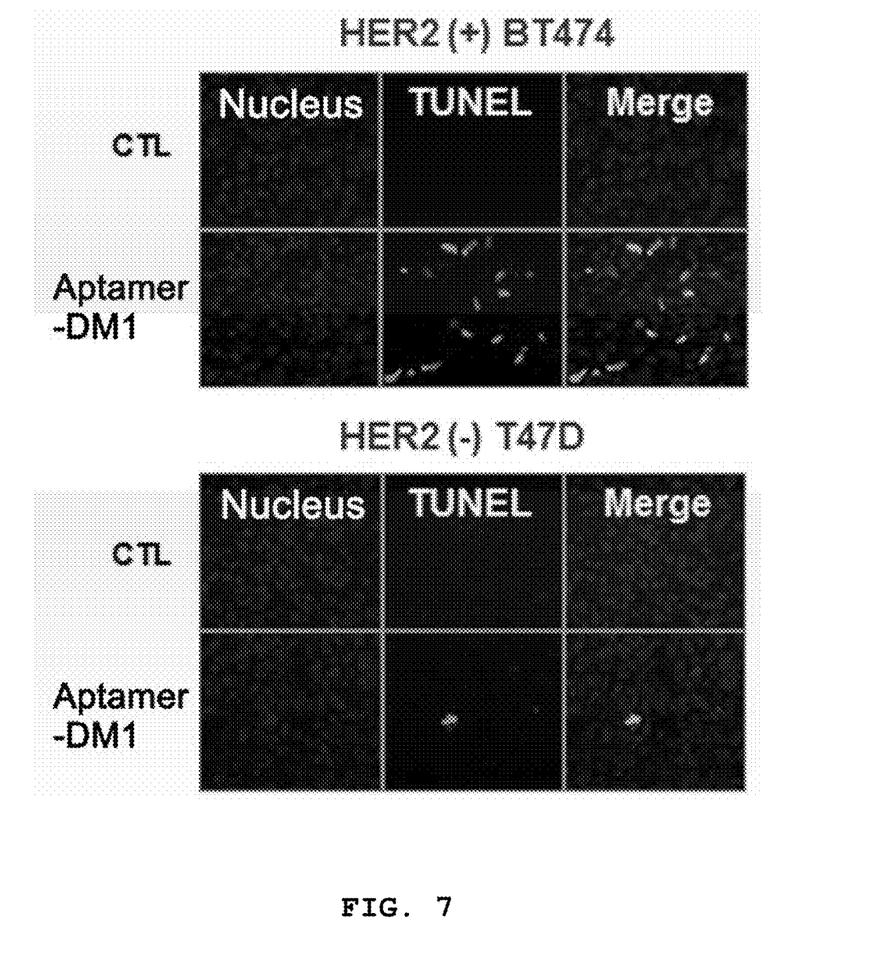
FIG. 7 shows images depicting the results of a TUNEL assay to evaluate the ability of the complex to selectively kill HER2-positive breast cancer cells in breast cancer disease animal models.

Evaluation of Ability of Aptamer-Anticancer Drug Complex to Selectively Kill HER2-Positive Breast Cancer Cells in Breast Cancer Disease Animal Model (1) To the fourth breast fat pads of immunodeficient 6-week-old female BALB/c nude mice, HER2-positive BT474 cancer cells ($3 \times 10^6$ cells) and HER2-negative T47D cancer cells ($3 \times 10^6$ cells) were transplanted, after which Aptamer-DM1 (1 mg/kg, 2 mg/kg, body weight) was intraperitoneally administered three times a week. Then, the tumor volume was measured for 18 days. The results are shown in FIG. 6, and the results of a TUNEL assay are shown in FIG. 7. The tumor volume (V) was measured using a caliper and calculated according to $V=(length \times width^2)/2$. In the TUNEL assay, the tumors were removed from the mice, fixed with 10% neutral-buffered formalin and embedded in paraffin. The 4 μm thick tissue section was mounted on a positively charged glass slide, deparaffinized with xylene, and dehydrated through a graded alcohol series. After antigen retrieval, the above tissue section was boiled in a citric acid buffer (pH 6.0) and immunofluorescence was performed. In situ TUNEL was performed on the above tissue section using a TUNEL kit (Roche Applied Sciences, Penzberg, GER), and the images thereof were obtained using a confocal scanning microscope.

(2) As shown in FIG. 6, Aptamer-DM1 significantly decreased only the growth of HER2-positive BT474 tumors. As shown in FIG. 7, based on the results of apoptosis through the TUNEL assay, Aptamer-DM1 effectively induced apoptosis only in the HER2-positive BT474 tumors. Thereby, Aptamer-DM1 can be confirmed to exhibit specific anticancer effects depending on the expression of HER2 in the animal models.

EXAMPLE 8

Establishment of Existing Drug-Resistant Cell Line and Evaluation of Properties Thereof (1) HER2-positive breast cancer BT474 cells were subcultured at intervals of 3 days using a culture medium containing 4 μg/ml of Trastuzumab, after which resistant clones, which were continuously exposed to Trastuzumab for a total of 8 months, were selected, thus establishing a Trastuzumab-resistant cell line (BT474-Tra).

Figure 8:
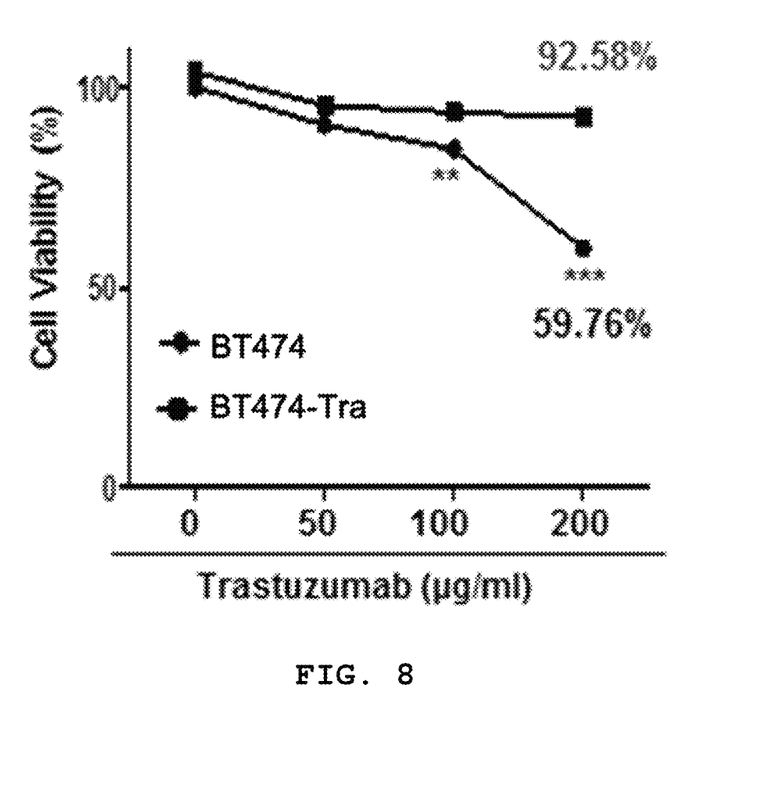
FIG. 8 shows the results of measurement of the cell viability of existing drug-resistant cell lines.
Figure 9:
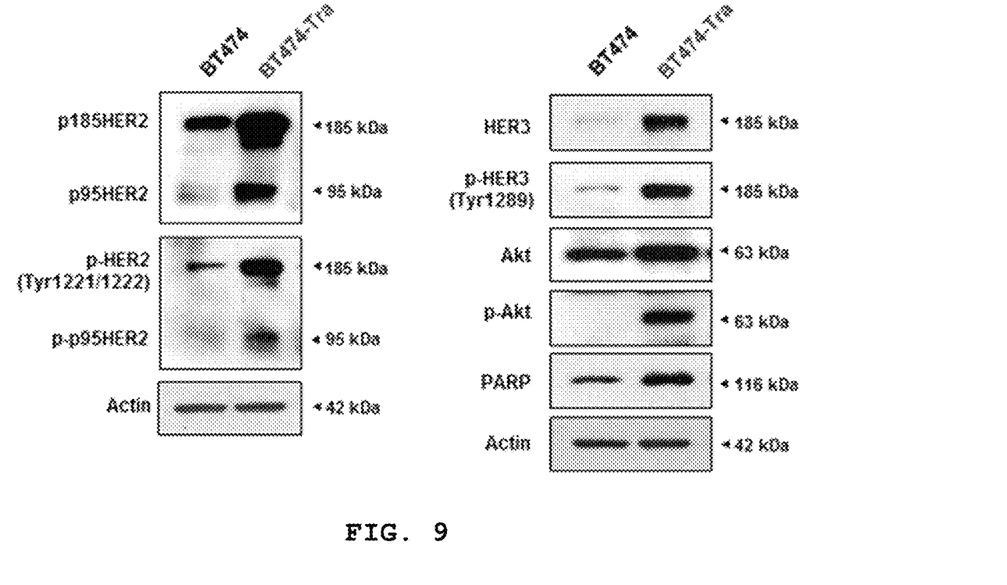
FIG. 9 shows images depicting the results of Western blot analysis of existing drug-resistant cell lines.

(2) BT474 and BT474-Tra cell lines were treated with Trastuzumab at a concentration of 0 to 200 μg/ml for 48 hr, after which the cell viability was measured. The results are shown in FIG. 8. For the BT474 and BT474-Tra cell lines, the expression of p185HER2, p95HER2, p-HER2, p-p95HER2, HER5, p-HER3, total-AKT, p-AKT, and PARP was analyzed via Western blot. The results are shown in FIG. 9. Cell viability was measured using a CellTiter 96* Aqueous One Solution Cell Proliferation Assay [MTS, 3-(4,5-dimethylthiazol-2-yl)-5-(3-carboxymethoxyphenyl)-2-(4-sulfophenyl)-2H-tetrazolium], and the amount of produced formazan was determined by measuring absorbance at 490 nm using a Spectramax Plus 384 microplate analyzer. In the Western blot, the above cells were lysed in a lysis buffer (30 mM NaCl, 0.5% Triton X-100, 50 mM Tris-HCl; pH 7.4) containing phosphatase and a protease inhibitor, and the supernatant was collected and then the protein was concentrated using a Bradford protein assay kit. 30 μg of the protein was subjected to SDS-PAGE and electrophoresed with a nitrocellulose membrane. The membrane was cultured overnight at 4° C. with primary antibodies diluted in bovine serum albumin (BSA) and then cultured with horseradish peroxidase (HRP)-conjugated rabbit IgG (1:3000-1:10,000). Signal intensity was measured using an Enhanced Chemiluminescence Kit and an X-ray film, and quantified with AlphaEaseFC software.

(3) As shown in FIG. 8, the Trastuzumab-resistant BT474 cell 10 line exhibited lower sensitivity to Trastuzumab than the BT474 cell line. As shown in FIG. 9, in the Trastuzumab-resistant BT474 cell line, the expression of full-length p185HER2, mutant p95HER2, and phosphorylated active-form p-HER2 and p-p95HER2 was considerably increased, and the expression of p-HER3/HER3 and p-Akt was remarkably increased.

EXAMPLE 9

Evaluation of Effect of Aptamer-Anticancer Drug Complex in Existing Drug-Resistant Cell Line (1) The Trastuzumab-resistant BT474 cell line and the JIMT-1 cell line derived from tumors of Trastuzumab-resistant patients were treated with a control (DMSO), DM1, Aptamer, and Aptamer-DM1 at a concentration of 10 nM for 72 hr, after which the expression of HER2, p95HER2, p-HER2, p-p95HER2, HER3, p-HER3, total-AKT, and p-AKT was analyzed via Western blot. The results are shown in FIG. 10.

Figure 10:
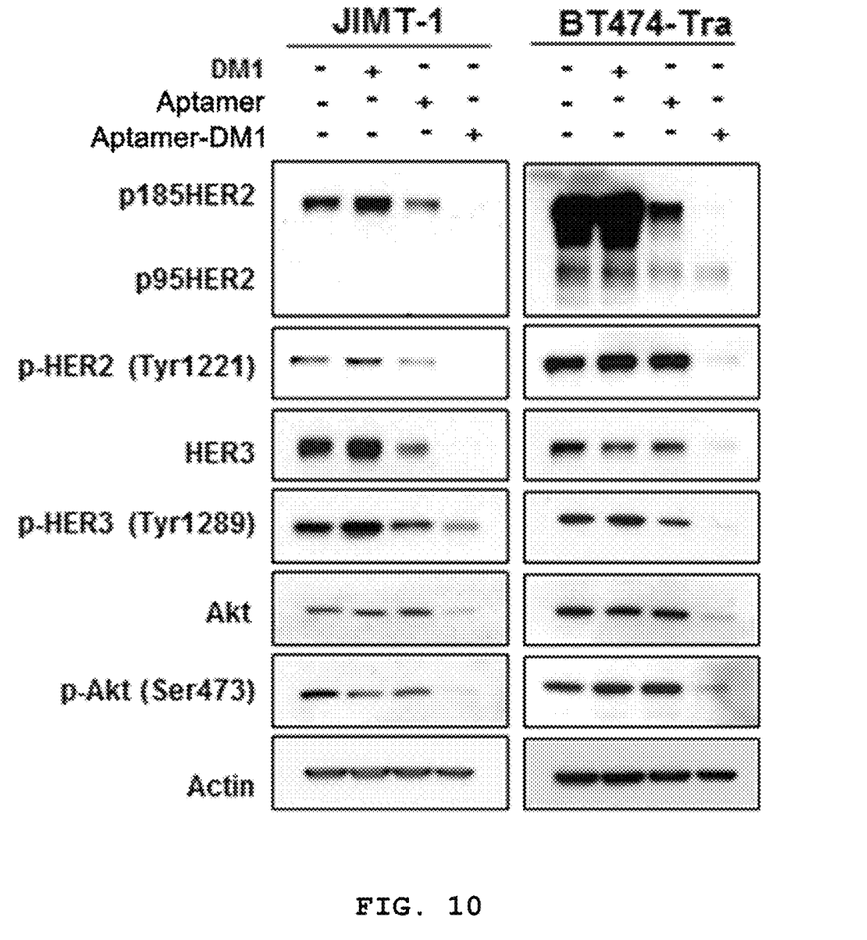
FIG. 10 shows images depicting the results of Western blot analysis to evaluate the effects of the drug complex on existing drug-resistant cell lines.

(2) As shown in FIG. 10, in the group treated with Aptamer-DM1, compared to the groups treated with the control, DM1, and Aptamer, the expression of not only full-length p185HER2 and active-form phospho-HER2 (Tyr1221) but also HER family compounds, such as HER3 and phospho-HER3, AKT and phospho-Akt (Ser 43), was significantly reduced. The expression of p95HER2, which is a mutant that causes resistance to Trastuzumab, was strongly inhibited in BT474-Tra cells. Thereby, the aptamer-anticancer drug complex can be confirmed to effectively overcome drug resistance, which is regarded as problematic in the treatment of HER2-positive tumors.

EXAMPLE 10

Figure 11:
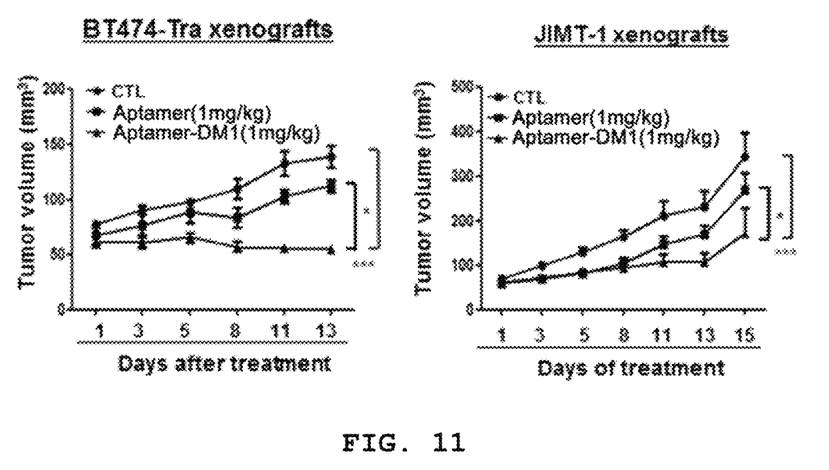
FIG. 11 shows the results of measurement of the tumor volume to evaluate the effects of the complex on existing drug-resistant disease animal models.
Figure 12:
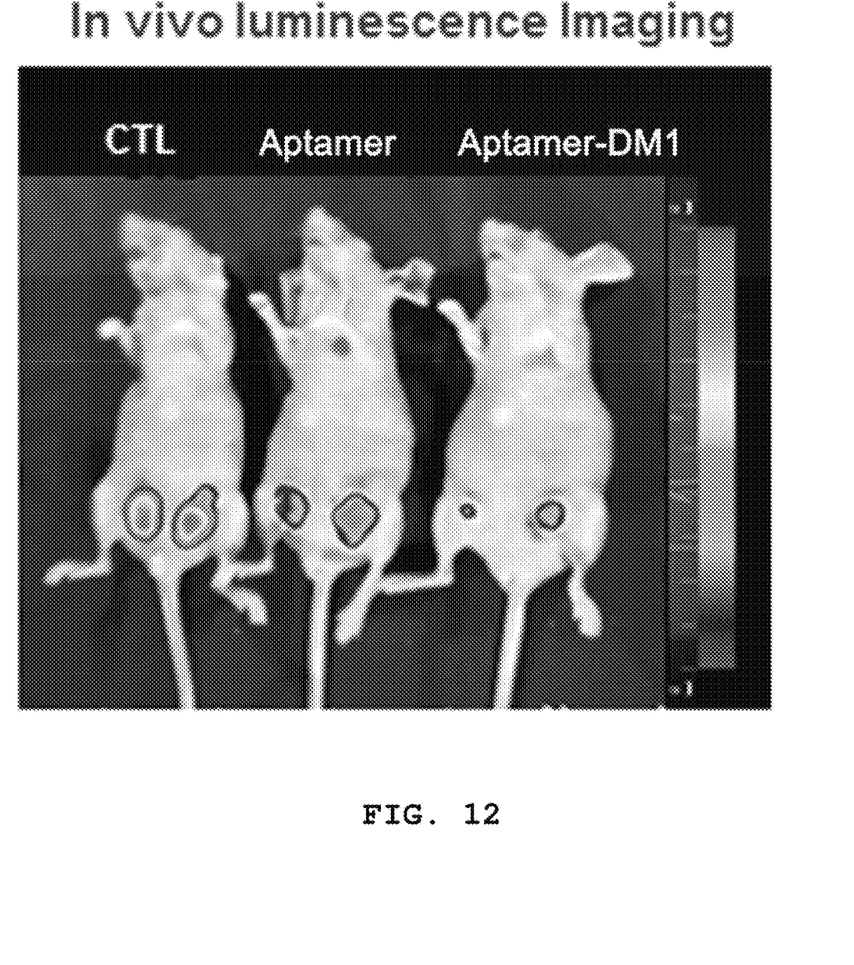
FIG. 12 shows an in-vivo bioluminescence image to evaluate the effects of the complex in existing drug-resistant disease animal models.

Evaluation of Effect of Aptamer-Anticancer Drug Complex in Existing Drug-Resistant Disease Animal Model (1) To the fourth breast fat pads of immunodeficient 6-week-old female BALB/c nude mice, BT474-Tra cells ($3 \times 10^6$ cells) and JIMT-1 cells ($3 \times 10^6$ cells) were transplanted to generate tumors, and each of Aptamer and Aptamer-DM1 was intraperitoneally administered (1 mg/kg, body weight). Thereafter, the tumor volume was measured for 15 days. The results are shown in FIG. 11, and the results of in-vivo bioluminescence imaging of JIMT-1-transplanted mice are shown in FIG. 12. In-vivo bioluminescence imaging was performed in a manner in which the mice were anesthetized and administered with 150 mg/kg of luciferin, after which the tumor size and the transition state were measured using a bioluminescence imaging system.

(2) As shown in FIG. 11, Aptamer-DM1 significantly reduced the tumor volume in both of the two resistant disease animal models transplanted with JIMT-1 and BT474-Tra. As shown in FIG. 12, luciferin intensity was remarkably decreased in the group administered with Aptamer-DM1. Thereby, Aptamer-DM1 can be confirmed to overcome drug resistance even in the resistant disease animal models.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of manufacturing a complex for cancer cell chemotherapy, comprising:
 a) preparing a nucleic acid aptamer consisting of the base sequence of SEQ ID NO:1 for specifically binding to HER2; and
 b) forming an aptamer-anticancer drug complex by reacting the aptamer with anticancer drug DM1;
 wherein the aptamer includes a thiol group introduced at the 3' terminal end and DM1 includes a thiol group such that a disulfide bond is formed between the aptamer and DM1.

2. The method of claim 1, wherein step a includes introducing a thiol group to the 3' terminal of the aptamer, performing 2'-0-methyl modification and activating the 3' thiol group by reaction with dithiothreitol in a triethylammonium acetate buffer.

3. The method of claim 1, wherein step b includes providing DM1 dissolved in dimethyl sulfoxide, and reacting the aptamer and the DM1 at a ratio of 1:1000 in a potassium phosphate buffer containing dimethyl sulfoxide (DMSO) and ethylenediaminetetraacetic acid (EDTA), thus forming the aptamer-anticancer drug complex.

4. The method of claim 2 wherein step b includes providing DM1 dissolved in dimethyl sulfoxide, and reacting the aptamer and the DM1 at a ratio of 1:1000 in a potassium phosphate buffer containing dimethyl sulfoxide (DMSO) and ethylenediaminetetraacetic acid (EDTA), thus forming the aptamer-anticancer drug complex.

* * * * *

SEQUENCE LISTING

<160> NUMBER OF SEQ ID NOS: 1

<210> SEQ ID NO 1
<211> LENGTH: 50
<212> TYPE: RNA
<213> ORGANISM: Artificial Sequence
<220> FEATURE:
<223> OTHER INFORMATION: HER2 aptamer

<400> SEQUENCE: 1
gggaggacga ugcgggacug uacggggcuc ugugcagacg acucgcccga                50